(12) United States Patent
Yoshimura et al.

(10) Patent No.: US 6,685,654 B2
(45) Date of Patent: Feb. 3, 2004

(54) HEALTH INDICATOR MEASURING DEVICE

(75) Inventors: Akira Yoshimura, Kashihara (JP); Toshihiko Machiyama, Kashihara (JP); Satoru Mori, Obu (JP)

(73) Assignee: Misaki Inc., Osaka (JP)

( * ) Notice: Subject to any disclaimer, the term of this patent is extended or adjusted under 35 U.S.C. 154(b) by 0 days.

(21) Appl. No.: 09/852,689

(22) Filed: May 11, 2001

(65) Prior Publication Data

US 2001/0053883 A1 Dec. 20, 2001

(30) Foreign Application Priority Data

May 12, 2000 (JP) ........................................ 2000-140531

(51) Int. Cl.$^7$ .............................................. A61B 5/103
(52) U.S. Cl. ........................ 600/587; 600/300; 600/547
(58) Field of Search ................................. 600/300, 547, 600/587

(56) References Cited

U.S. PATENT DOCUMENTS

| 6,168,563 | B1 | * | 1/2001 | Brown ........................ 600/301 |
| 6,398,740 | B1 | * | 6/2002 | Lavery et al. ............... 600/300 |
| 6,440,068 | B1 | * | 8/2002 | Brown et al. ............... 600/300 |
| 6,450,955 | B1 | * | 9/2002 | Brown et al. ............... 600/300 |

* cited by examiner

Primary Examiner—Robin O. Evans
(74) Attorney, Agent, or Firm—Wenderoth, Lind & Ponack, L.L.P.

(57) ABSTRACT

This health indicator measuring device includes an arithmetical operation means for computing data of a lean body per body height or a data of a body fat per body height on the basis of the respective data of body weight, body fat and body height. The health indicator measuring device has the capability of measuring a qualitative aspect or a quantitative aspect of muscle of a person to be measured and outputting indicators of a health year equivalent and an advice data on practical fitness for health related to the function of the body measured.

9 Claims, 26 Drawing Sheets

HEALTH INDICATOR MEASURING DEVICE

BACKGROUND OF THE INVENTION

1. Field of the Invention

The present invention relates to a device for outputting various characteristic indicators closely related to health condition of a human being.

2. Prior Art

A body weight and a ratio between body weight and body height are generally known as characteristic indicators of health condition of human being. Recently, a proportion of body fat to the body weight has come to be added as one of the characteristic indicators of health condition. The characteristic indicators of body weight, body height and body fat are referred to as the physical indicators.

Recently, the proportion of the body fat to the body weight has come to be determined by measuring impedance of one's body and the body height and calculating the body fat from those values on the basis of a certain experimental formula. The terminology of "body fat" used herein is intended to cover a weight of body fat for the impedance of the body or a proportion of the body fat to the body weight. The terminology of "lean body mass" used herein is intended to cover a weight of lean body obtained when the body fat is subtracted from the body weight, or its proportion to the body weight.

The physical indicators (body weight, body height and body fat) are closely related to the condition of one's health, and there are difficulties in judging the condition of one's health from those physical indicators only.

The conditions of one's health are closely related to the general organic parts of the body and the physical capacities, including the function of the body as well as the physical indicators. Hence, only the measurement of the physical indicators can only take the results of the one's current physical indicators but cannot go far enough to evaluate the function of the body.

Additionally, this conventional way of measuring only those physical indicators is not sufficient to give advice or suggestions to users on what and how to improve in order to grow strong in health.

Further, from the viewpoint of, for example, how to reduce the body fat, the conventional way of measuring only the physical indicators is inadequate.

Suppose there is a person who has a lot of body fats and strong muscles, for example. That person can be considered to burn much calories and thus grow healthfully. Thus, even if a person has a lot of body fats, that does not directly mean that he/she is not healthy.

Conversely, even if he/she has a small amount of muscles, if the muscles have excellent capacities, he/she can be considered to be healthy.

From this viewpoint, the proportion of the muscles to the body weight or the lean body mass can be said to be a critical indicator. In addition, instantaneous power and staying power of the muscles can also be said to be critical indicators of the health condition.

The existing devices can neither measure these critical indicators in a simple and easy manner nor explain what the measurement results mean in specific terms or give practical advice on what the user should be done for his/her health in the future.

Generally, the functions of the body, such as the instantaneous power and the staying power of the muscles, decline with age, while however, the physical capacities can be kept or improved by training. There are no existing devices having the capability of making comparison between the functions of the body and the standard physical indicators at selected ages so that a health year equivalent of the functions of the body of the person measured can be determined from the difference therebetween or a general health year of the person measured can be derived from the preset age-specific standard indicators containing the comparative data, to give it to the person measured in a simple and easy manner.

SUMMARY OF THE INVENTION

Accordingly, the present invention has been made with the aim to provide a device capable of generally grasping the health condition of a person measured and outputting the shade of meaning and a practical advice for his/her health in the future.

A health indicator measuring device according to the present invention comprises an arithmetical operation means for computing data of a lean body per body height or data of a body fat per body height on the basis of the respective data of body weight, body fat and body height. The data of the lean body per body height is an indicator of a lean body mass per body height. The data of the body fat per body height is an indicator of a body fat weight per body height.

The health indicator measuring device includes a physical function measuring means to measure function of the body and an output means to output a function indicator computed on the basis of the function of the body measured.

The functions of the body include total physical response time, instantaneous power, staying power, and cardiopulmonary function.

Further, the physical function measuring means is intended to measure a qualitative aspect or a quantitative aspect of muscle of a person to be measured. The qualitative aspects of the muscle include indicators such as total physical response time, total physical staying power, muscle strength, instantaneous power and staying power of muscle. The quantitative aspects of muscle include indicators related to the muscle, such as the lean body mass.

With this construction, not only the conventional measurements of the body weight and body fat but also more specific indicators, such as the muscle strength and the total physical response time, can be measured so that further specific indicators for health can be grasped.

The output means of the health indicator measuring device according to the present invention is intended to compare the function indicator computed on the basis of the function of the body measured with preset standard indicators, to output data of the difference therebetween. With this construction, the function indicator as was computed is compared with a preset standard indicator for an age of the person to be measured, and the data of the difference is the difference therebetween or a proportion of the difference to the total function. Thus, the difference can be determined by comparing the function indicator computed on the basis of the function of the body with the standard indicator.

The output means is preferably intended to compare the function indicator computed on the basis of the function of the body measured with preset standard indicators at selected ages, to output an equivalent age to a closest indicator as an indicator of a health year equivalent. With this construction, a health year on the standard indicator equivalent to the data of the body fat per body height of the person to be measured, the function of the body and the quantitative or qualitative aspects of the muscle is output. Thus, the person to be measured can know from his/her indicators about to which year his/her indicators are equivalent on the standard scale in the form of the health year equivalent.

Further, the output means has the capability of outputting an advice data on a practical fitness for health related to the function of the body measured. This advice data suggests the point to notice for health in the future in the concrete form.

DETAILED DESCRIPTION OF THE PREFERRED EMBODIMENTS

In the following, the health indicator measuring device according to the present invention will be described in detail with reference to the accompanying drawings illustrating the preferred embodiments.

Figure 1:
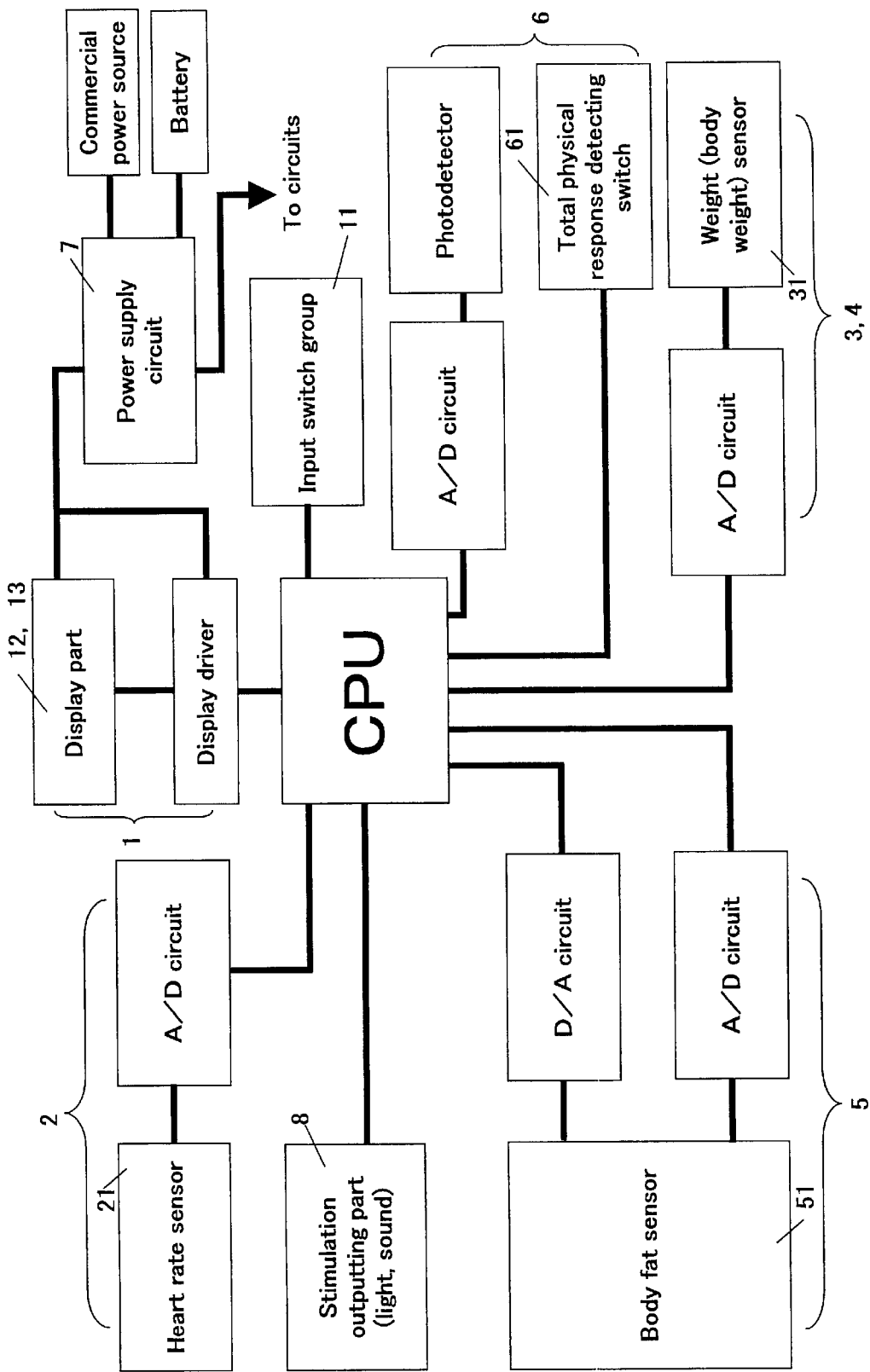
FIG. 1 is a block diagram of a health indicator measuring device, according to a preferred embodiment of the present invention.

A health indicator measuring device according to the present invention comprises, as shown in FIG. 1 of a block diagram of the overall construction, a display control part 1 for mainly controlling various set-up operations and displaying various indicators, a heart rate measuring part 2 using a finger-wearable or earlap-wearable photosensor 21 of light transmission type or light reflection type, a body weight measuring part 3 including a load sensor 31 for detecting a body weight of a person to be measured who mounts a measuring platform, a muscle strength measuring part 4 for measuring muscle strength of the person to be measured by pulling, a body fat measuring part 5 including electrodes 51 contactable with soles of the person's feet to measure the impedance of the body and convert it to the body fat, a total physical response time measuring part 6 including a response detecting sensor 61 for detecting that the person to be measured responds to particular stimulation released from the display control part 1, connecting cords connecting between the respective measuring parts and the display control part 1, and a power source 7 for supplying electric power to the respective measuring parts and the display control part 1.

Figure 2A:
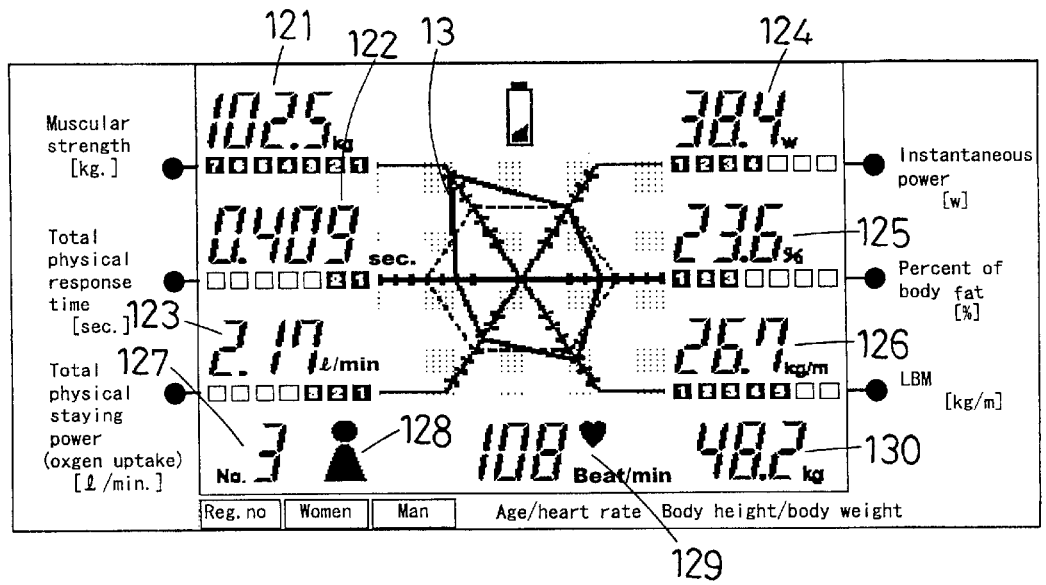
FIG. 2 is an illustration of a display screen.
Figure 2B:
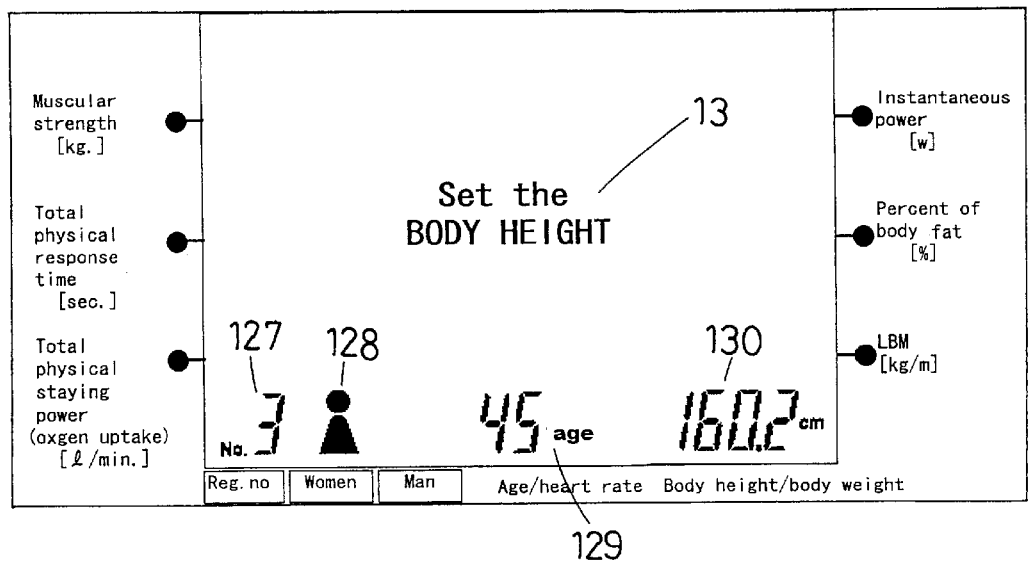
Figure 3A:
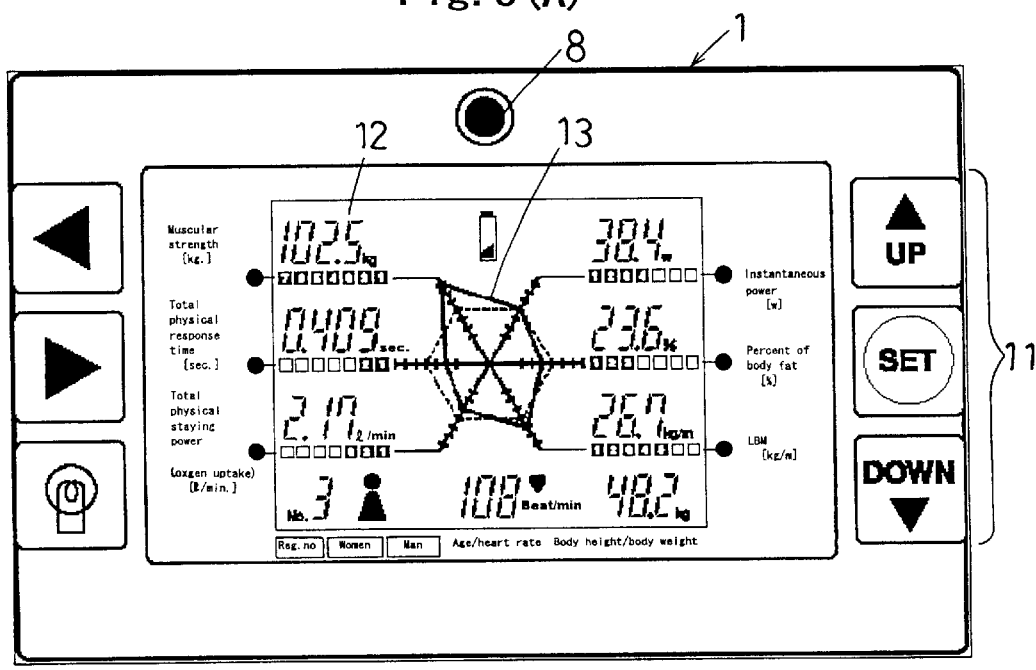
FIG. 3 is an illustration of an operation display.
Figure 3B:
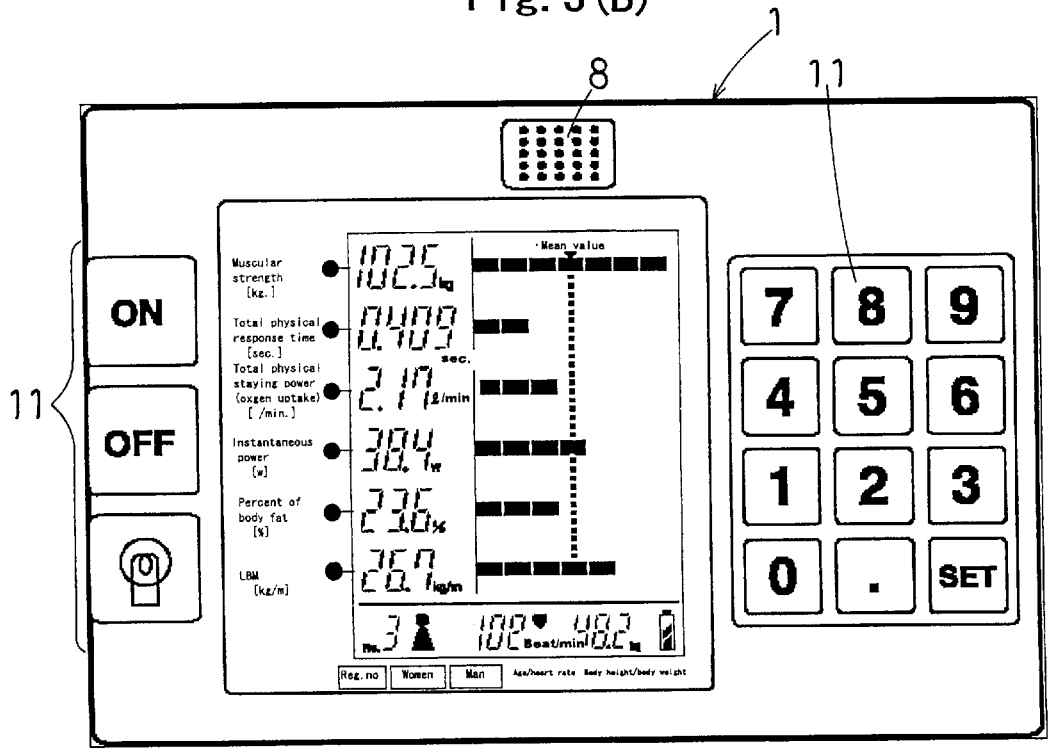

The display control part 1 includes a group of operating switches 11, a character display screen 12, a graphic display screen 13, and a stimulation outputting means 8 for outputting the stimulation via sound or light, as shown in FIGS. 2 and 3.

The person to be measured operates the group of operating switches 11 as shown in FIG. 3 to enter his/her body height, age, sexuality, etc. These data are stored and retained for each registration number. Once stored and retained, the data can be recalled by simply specifying the registration number, to eliminate the need to reenter the prompted data.

The character display screen 12 comprises, as shown in FIG. 2(A), a muscle strength display part 121, a total physical response time display part 122, a total physical staying power display part 123, an instantaneous power display part 124, a body fat percent display part 125, LBM (lean body mass per body height as mentioned later) display part 126, a registration number display part 127, a sexuality display part 128, an age/heart rate display part 129, and a body height/body weight display part 130.

The graphic display screen 13 has the capabilities of displaying a radar chart as shown in FIG. 2(A) and illustrative characters to prompt the user to enter the data (e.g. "Set the body height") as shown in FIG. 2(B).

Figure 4:
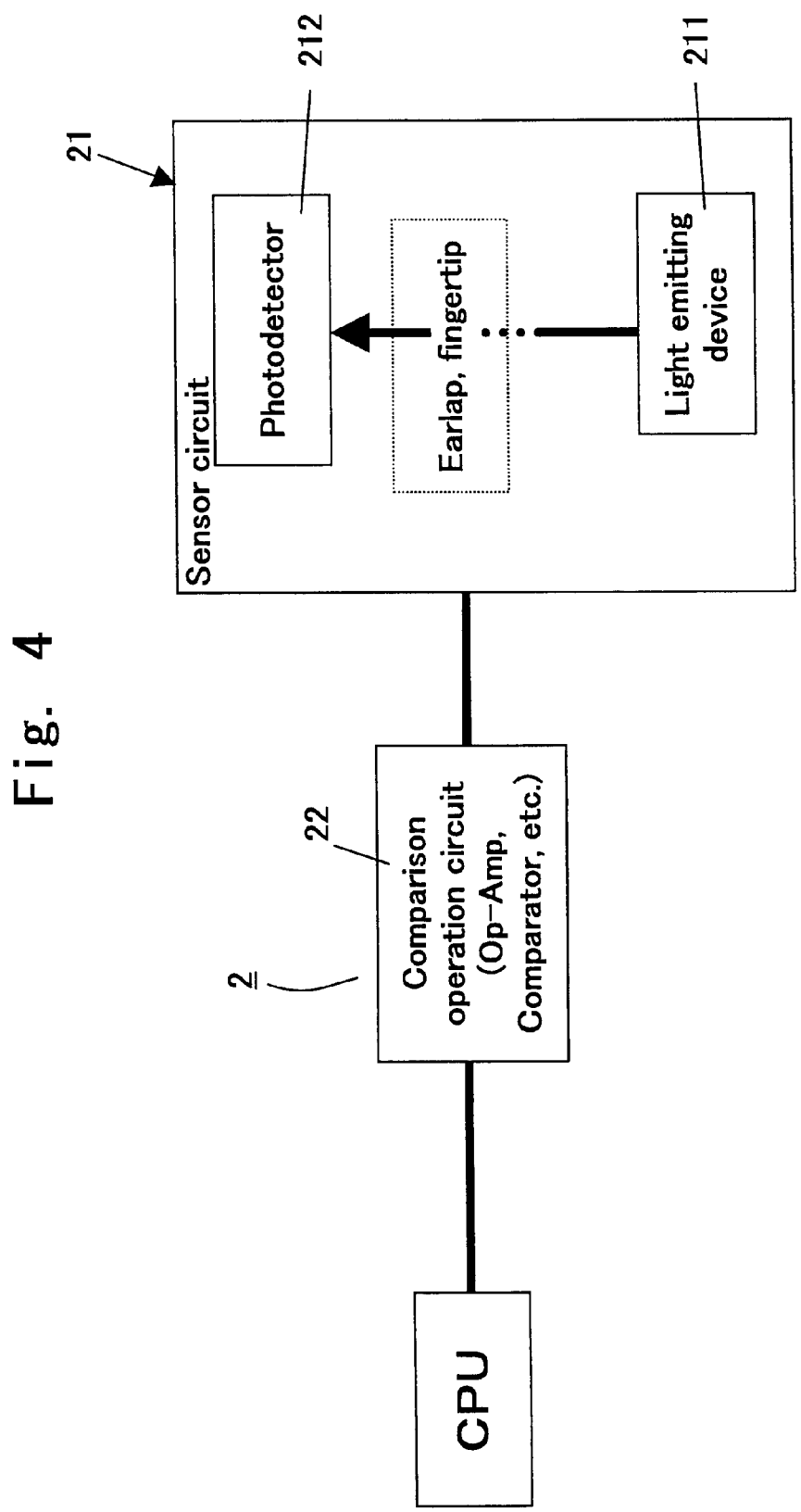
FIG. 4 is a diagram showing a substantial part of a heart rate measuring part.

The heart rate measuring part 2 includes, as shown in FIGS. 1 and 4, a photosensor 21 that is so constructed that the light from a light emitting device 211 can transmit or reflect a fingertip or an earlap to be incident on a photodetector 212, and a comparison operation circuit 22 to compare the electric signals from the photosensor 21 with specified thresholds and extract the heart beat signals. The heart beat signals are input to CPU and are converted to the heart rate therein.

In the body weight measuring part 3, when the person to be measured mounts the measuring platform 30, the electric signals corresponding to the body weight measured by a known load sensor 31 are converted to digital signals by an A/D convertor circuit 32 and are input to the CPU.

Figure 5A:
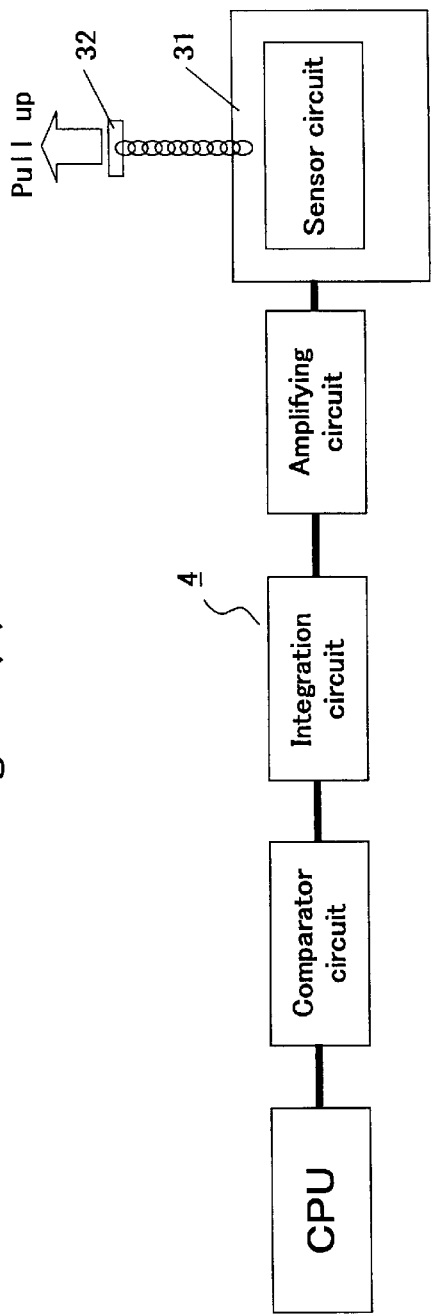
FIG. 5 is a diagram showing a substantial part of a body weight measuring part.
Figure 5B:
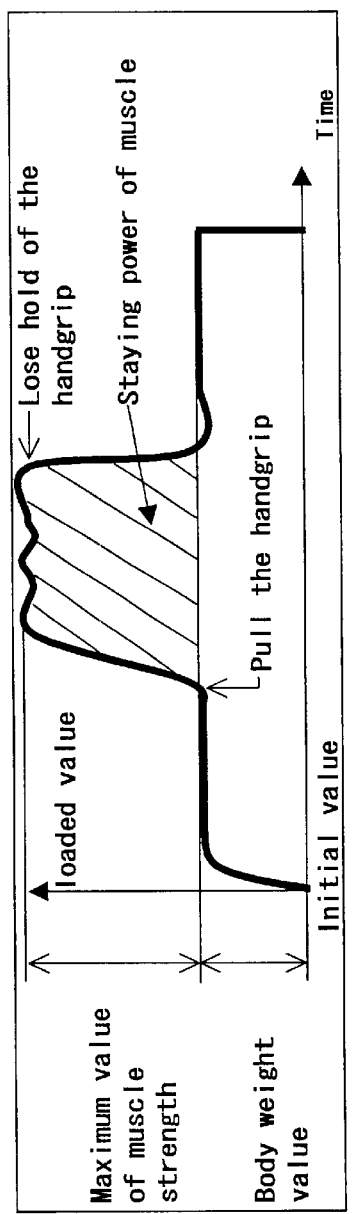

In the muscle strength measuring part 4, the back strength of the person to be measured is measured by a handgrip or equivalent of an operating means 32 (e.g. a chain secured to a base plate) being pulled by the person to be measured mounting the measuring platform 30, to apply a load to the load sensor 31 arranged for use with the body weight measuring part 3, as shown in FIG. 5.

The signals output from the load sensor 31 include those corresponding to the values of the body weight and the muscle strength, as shown in FIG. 5. Specifically, when the person to be measured mounts the measuring platform 30, the output signals from the load sensor 31 correspond to the body weight itself. As the measurement of the muscle strength starts, the load increases gradually, and when the measurement of the muscle strength is ended, the load comes back to the body weight again.

Thus, the value of the muscle strength is calculated by subtracting the body weight from the load measured.

Figure 24:
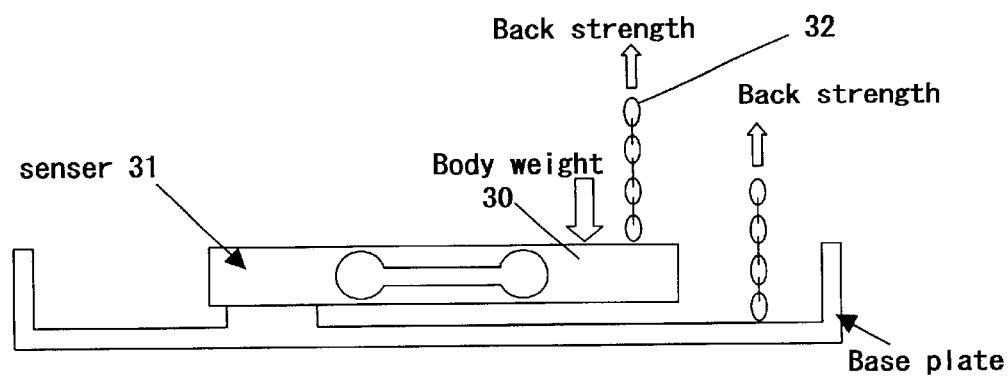
FIG. 24 is a perspective view of another preferred embodiment.

Alternatively, the difference between the body weight of the person to be measured and the back strength can be measured by pulling the handgrip or equivalent of the operating means 32 (e.g. the chain secured to the load sensor 31) being pulled by the person to be measured mounting the measuring platform 30, as shown in FIG. 24. Thus, the back strength can be measured from the difference therebetween and the body weight.

Figure 25:
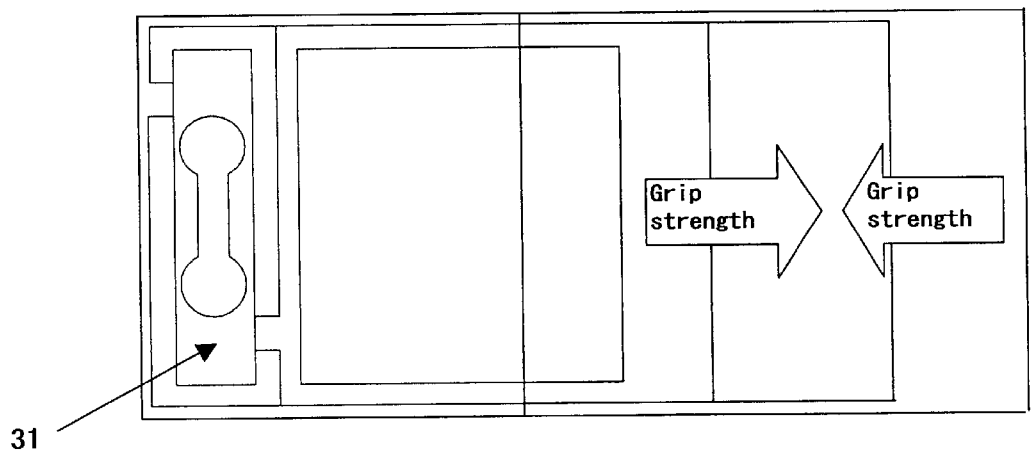
FIG. 25 is a perspective view of another preferred embodiment.
Figure 26:
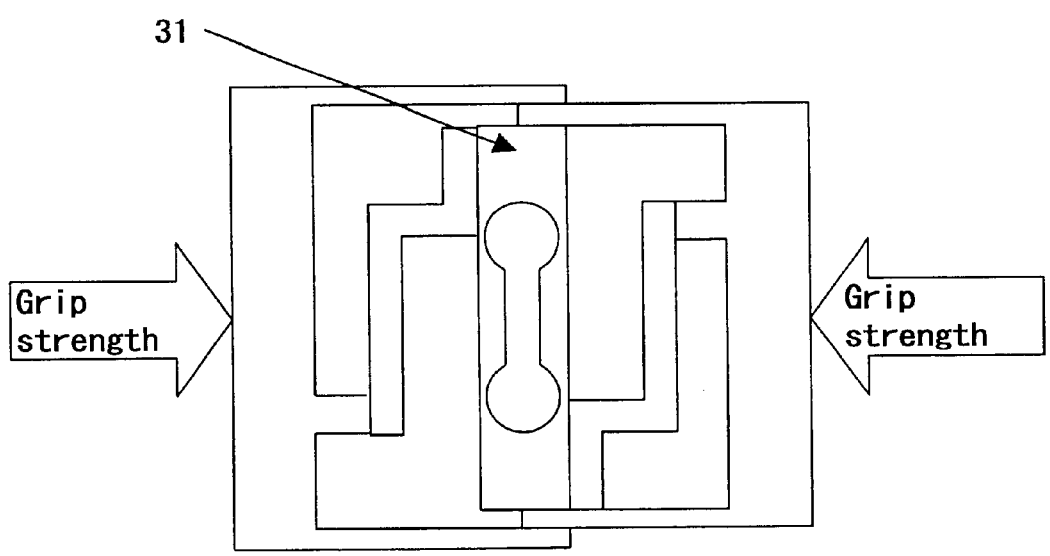
FIG. 26 is a perspective view of another preferred embodiment.

Additionally, grip strength can also be measured by deforming the load sensor 31 by gripping, as shown in FIGS. 25 and 26.

The body fat measuring part 5 includes a body impedance measuring part 52 to measure the impedance of the body by the pass of a weak electric current from soles through lower limbs of the person to be measured, standing with his/her soles contacting with the electrodes arranged in the measuring platform 30 or separately arranged therefrom. The signals of the impedance of the body thus measured are input to the CPU and are converted to the percent of the body fat on the basis of a specified experimental formula. The conversion is performed with high precision by use of a variety of data including body weight, body height, age, sexuality, etc., in addition to the impedance of the body.

In the total physical response time measuring part 6, the start time of jumping of the person to be measured and the finish time thereof are detected by the change of outside light that is incident on a response detecting sensor 61 arranged in a jumping board 60.

Specifically, the response detecting sensor 61 uses a photodetector such as a CdS, a phototransistor and a photodiode. It detects the momentary change of outside light incident from a lighting opening in the jumping board 60 from the state of the light being shielded by a foot of the person to be measured to the state of the light being incident from the lighting opening by the jumping of the person to be measured. In the illustrated embodiment, the A/D conversion is performed by the comparison operation circuit 63 on the basis of a reference voltage output from a reference voltage circuit 62 and then the signal conversion to the digital signals is converted to passage of time by the CPU's timer function. Thus, the start time of jumping and the finish time thereof are detected.

The start time of the jumping and the finish time thereof can alternatively be detected by detecting the loaded state and the instant of the load being removed, by use of switches arranged in the jumping board 60.

Figure 6A:
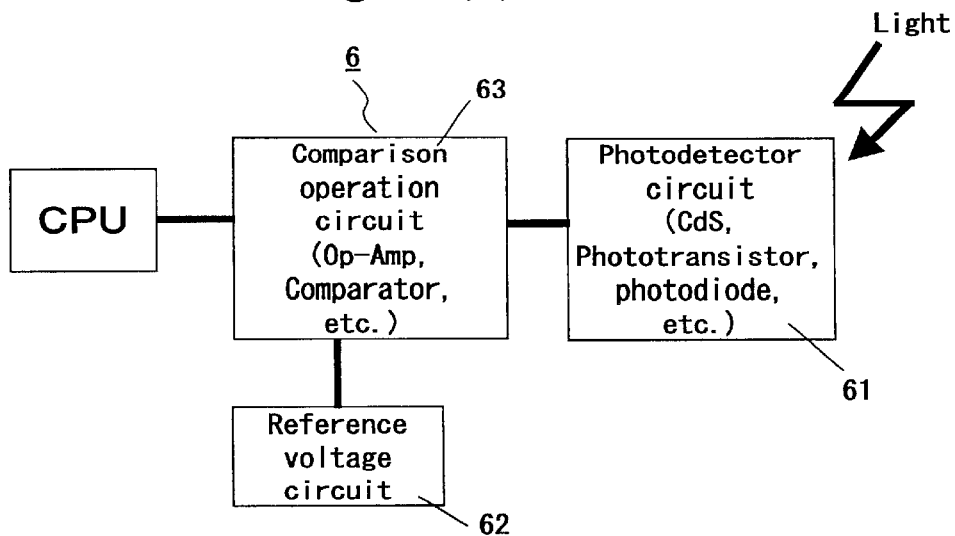
FIG. 6 is a diagram showing a substantial part of a total physical response time measuring part.
Figure 6B:
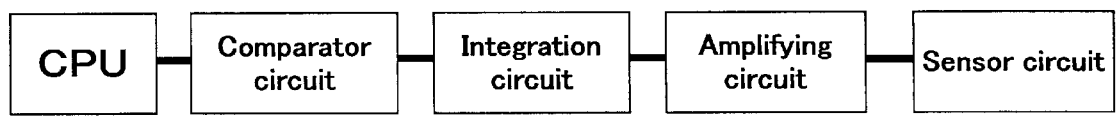
Figure 6C:
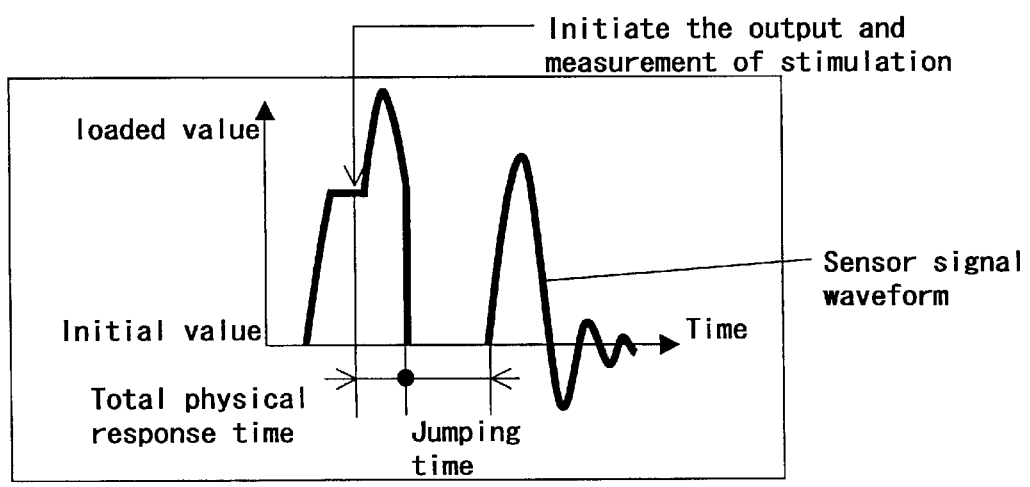

Further, the start time of the jumping and the finish time thereof can also be detected by monitoring the output signals from the load sensor 31 by use of the CPU, as shown in FIG. 6.

The items of the health indicator measuring device of the present invention will be explained with reference to TABLE 1.

Input items and units thereof are shown in (i) of TABLE 1; measurement items and units thereof are shown in (ii) of TABLE 1; and display items and unit thereof are shown in (iii) of TABLE 1.

TABLE 1

| | Item | Unit | |
|---|---|---|---|
| | i. Input item | | |
| 1 | Age (Date of birth) | Y/O | |
| 2 | Body height | m(cm) | |
| 3 | Sexuality | | |
| | ii. Measurement item | | |
| 1 | Body weight | Kg | |
| 2 | Impedance of body | Ω | |
| 3 | Total physical response time | Sec. | |
| 4 | Heart rate | Beat/Min. | |
| 5 | Muscle strength | Kg | |
| | iii. Display item | | |
| | Item | Unit | Calculation |
| 1 | Percent of body fat | % | As usual |
| 2 | LBM (Lean body mass per body height) | Kg/m | (Body weight × (1-(percent of body fat/100))/Body height |
| 3 | Total physical response time | Sec. | Measured value |
| 4 | Total physical staying power | 1/min. | Cf. Footnote of iv |
| 5 | Muscle strength | Kg | Measured value |
| 6 | Instantaneous power | W | Integrated value of treading load/Total physical response time |
| 7 | Staying power of muscle | Kg/sec. | Integrated value of muscle strength during a definite period of time/a definite period of time |
| Final display | Health evaluation health year equivalent | Y/O | Cf. Footnote of iv |

The terminology of "LBM" in the display item is a lean body mass per body height, which is calculated by the formula of (body weight × (1-(percent of body fat/100))/body height. The muscle forms a proportion of about 50% of the LBM by amount and the rest is made up of a variety of internal organs, bones, and blood. Accordingly, the LBM undergoes no drastic change in amount, except the muscles, which indicates that increase or decrease of the LBM means increase or decrease of the amount of muscles. Therefore, the LBM can be divided by the body height to adjust differences among individuals, for the sake of equal comparison. Also, it is used as the indicator of the amount of muscles.

Figure 27:
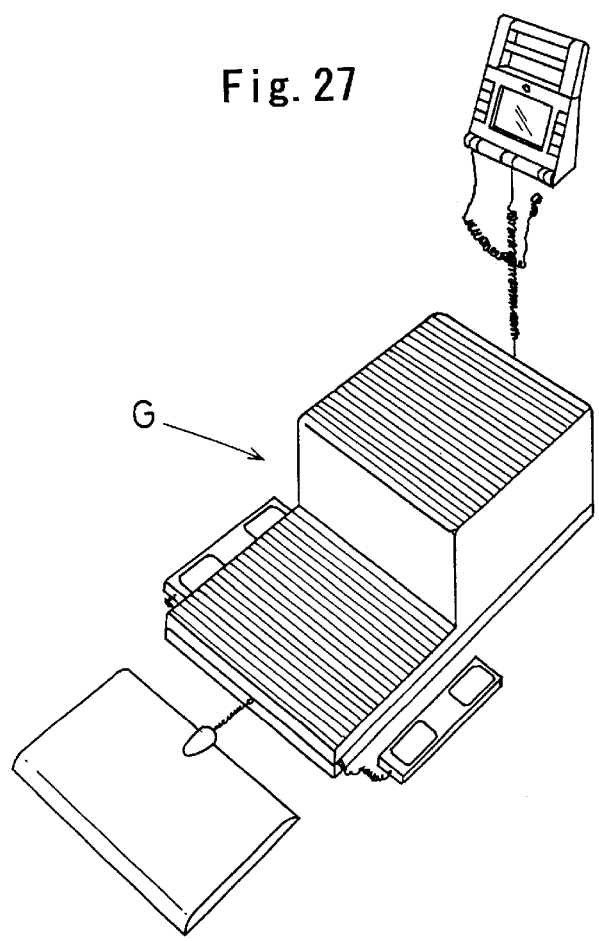
FIG. 27 is a perspective view of another preferred embodiment.
Figure 28:
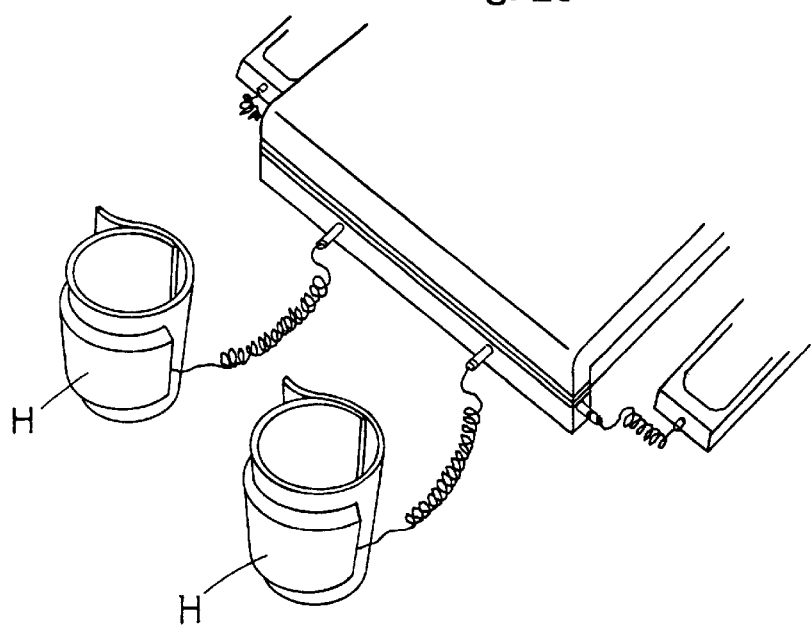
FIG. 28 is a perspective view of another preferred embodiment.

For the total physical staying power, work units are estimated from the body weight and a treading (moving up and down the platform) pitch, and oxygen uptake corresponding to the estimated work units is determined. The load on the body is made to gradually increase in three stages, whereby the heart rate that is increased in parallel with increase in load is measured. From the heart rate and the oxygen uptake a linear expression is derived by use of a minimum square. The maximum heart rate is estimated from (200−age). The maximum oxygen uptake corresponding to the maximum heart rate is estimated from a specified conversion expression. To measure the total physical staying power, the mechanism having steps for the treading as shown in FIG. 27 may be used. To measure the kinetic momentum, plummets containing acceleration sensors may be fitted to the ankles, as shown in FIG. 28.

The oxygen uptake can also be estimated from the LBM by utilizing the correlation between the oxygen uptake and the LBM, without measuring the heart rate during the treading.

The muscle strength can be measured by use of the mechanism as shown in FIGS. 5, 21 and 22, though it can be measured by use of the function of a known back-dynamometer. It can alternatively be measured by use of a grip dynamometer, as shown in FIGS. 25 and 26. A peak value of the treading load on the platform at the jump can also be measured.

The instantaneous power is determined by the load in the jump being measured to integrate the loads during the period of time from the moment at which the stimulus is applied to the moment at which the feet move away from the platform and being divided by the total physical response time. Accordingly, the larger the treading load becomes, the more the instantaneous power increases, and the shorter the total physical response time becomes, the larger the instantaneous power becomes. In the opposite case, the instantaneous power becomes smaller.

The health year equivalent is determined by comparing the data obtained from the respective measurement items with the standard values for each age obtained by separate searches, and the age of the standard value comparable to the data of the person measured is displayed as the health year equivalent. Accordingly, if his/her health year equivalent is younger than the actual age, then he/she can be considered to be better in health than the standard health condition.

Figure 7:
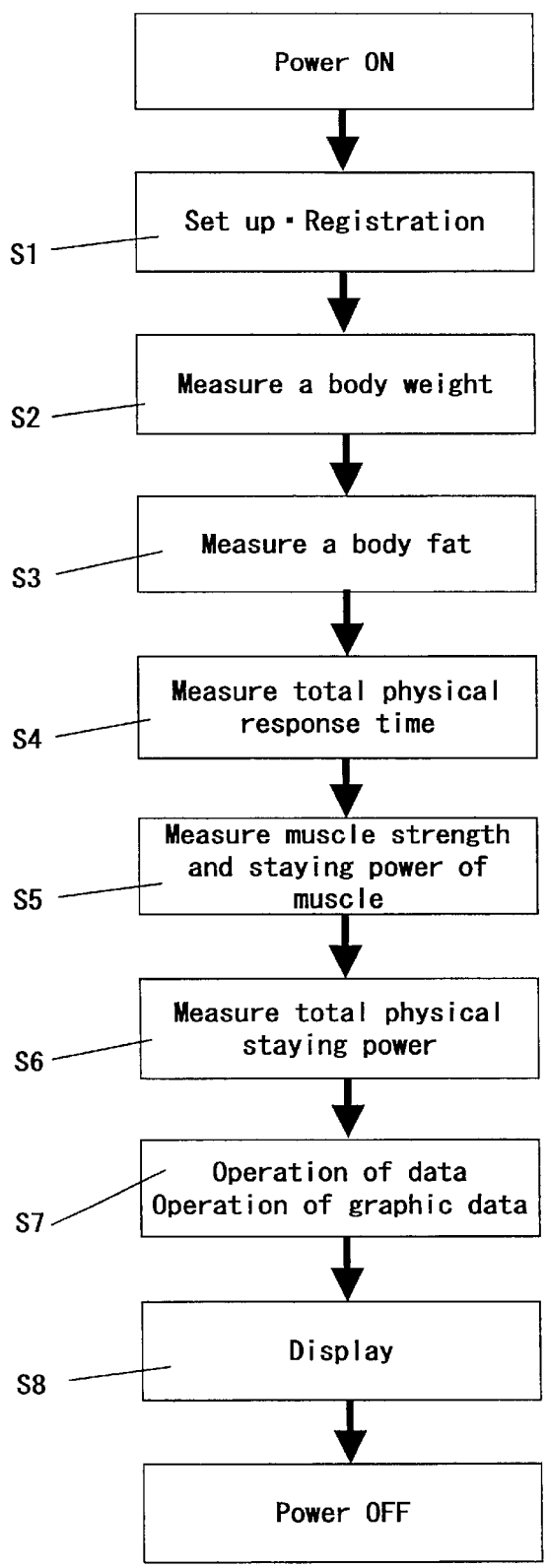
FIG. 7 is a flowchart of a measuring procedure.

Now, an example of the actual measuring procedure will be described with reference to the flowchart of FIG. 7.

Figure 8:
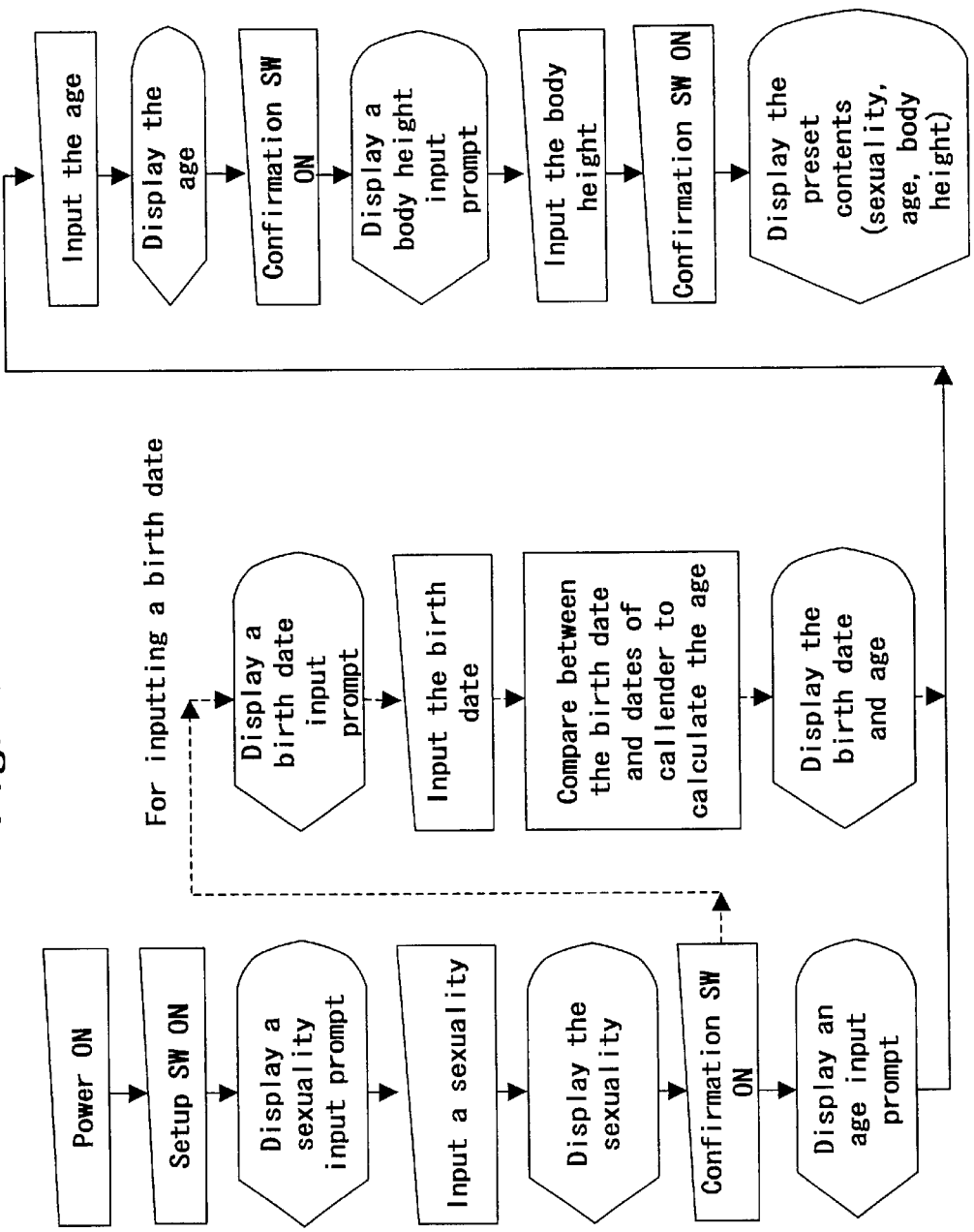
FIG. 8 is a detailed flowchart of the measuring procedure.

First, the power is turned on, and registration of a person to be measured takes place in the step S1. For an already registered person, the registration number is just required to be specified. For an unregistered person, the sexuality, body height and age are input for registration. An example of the detailed procedure is shown in FIG. 8.

Figure 9:
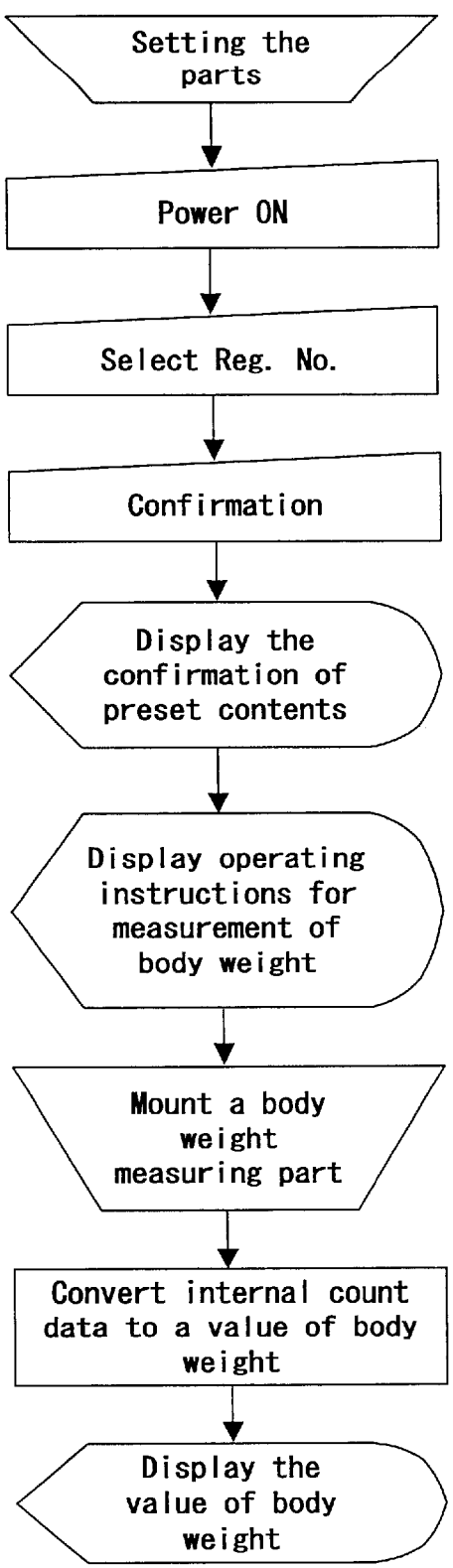
FIG. 9 is a detailed flowchart of the measuring procedure.

Then, in the body weight measuring procedure of the step S2, the body weight of the person to be measured is measured and stored by the body weight measuring part 3. An example of the detailed procedure is shown in FIG. 9.

Figure 10:
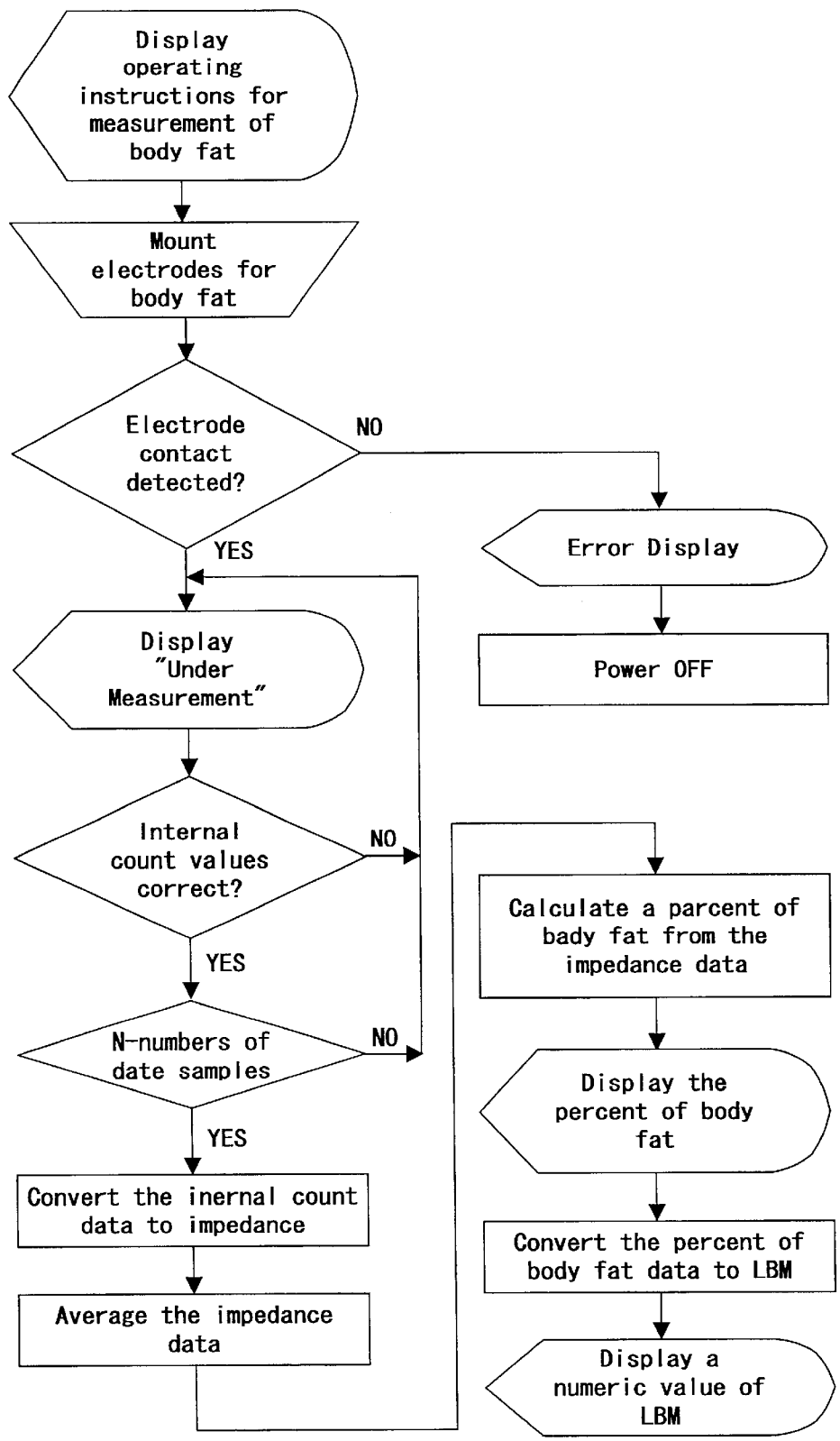
FIG. 10 is a detailed flowchart of the measuring procedure.

Then, in the body fat measuring procedure of the step S3, the body fat of the person to be measured is measured and stored by the body fat measuring part 5. An example of the detailed procedure is shown in FIG. 10.

Figure 11:
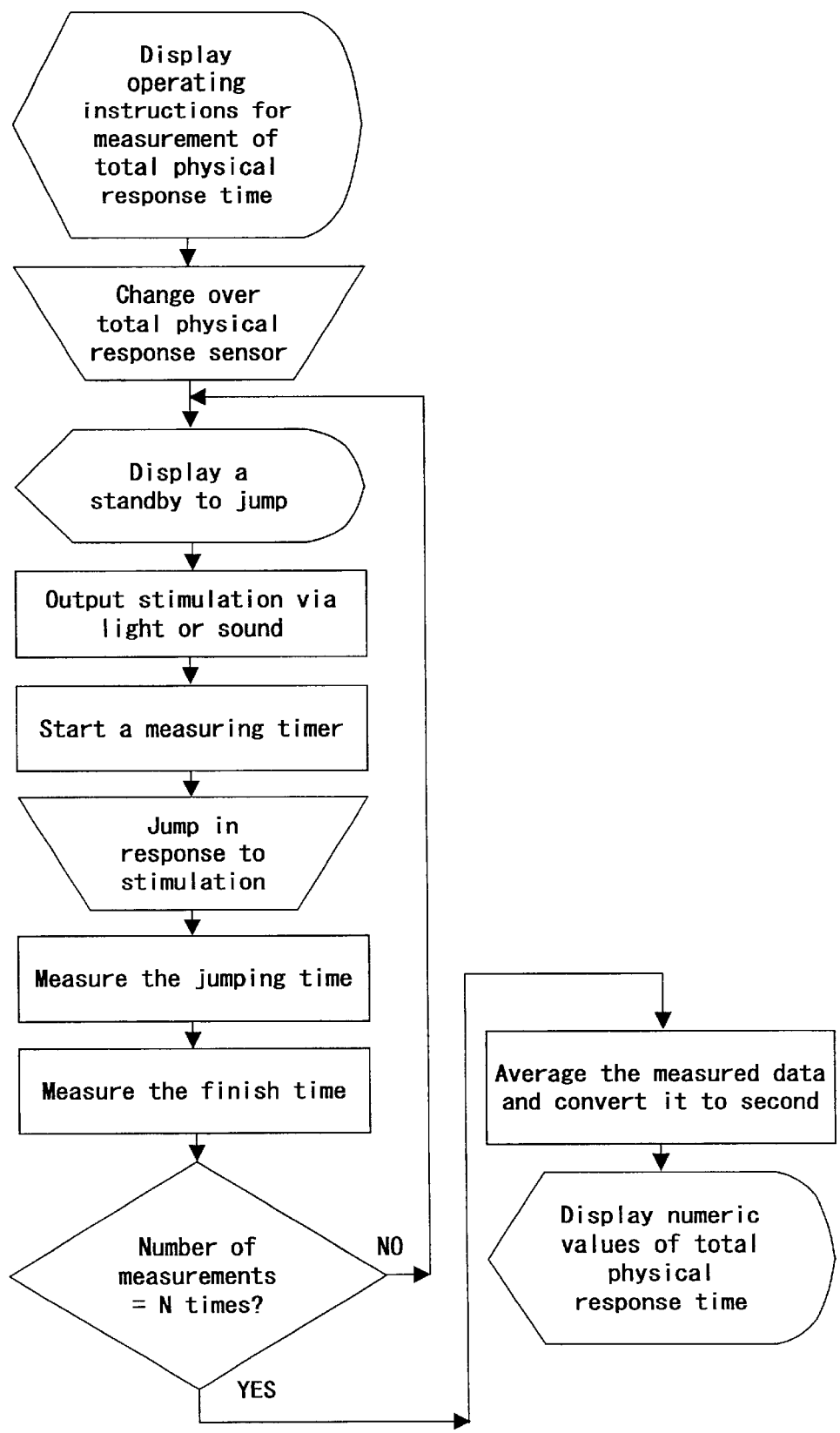
FIG. 11 is a detailed flowchart of the measuring procedure.

Then, in the total physical response time measuring procedure of the step S4, the total physical response time of the person to be measured is measured and stored by the total physical response time measuring part 6. An example of the detailed procedure is shown in FIG. 11.

Figure 12:
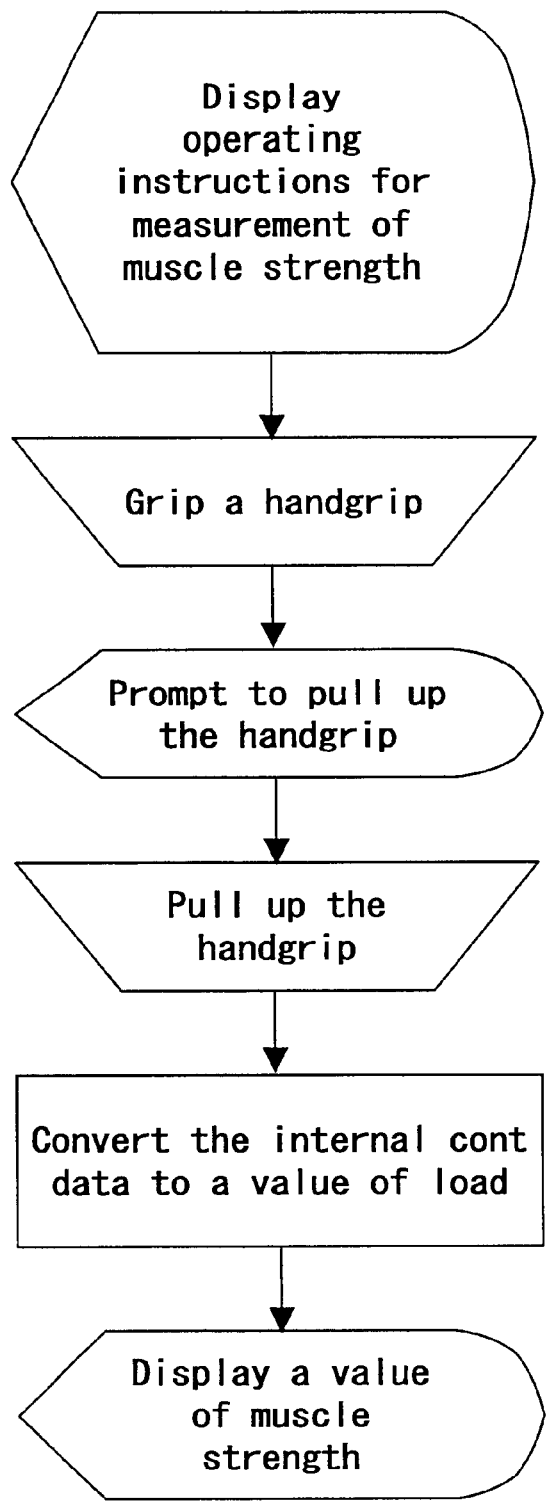
FIG. 12 is a detailed flowchart of the measuring procedure.

Then, in the muscle strength/muscle staying power measuring procedure of the step S5, the muscle strength of the person to be measured is measured and stored by the muscle strength measuring part 4. An example of the detailed procedure is shown in FIG. 12.

Figure 13:
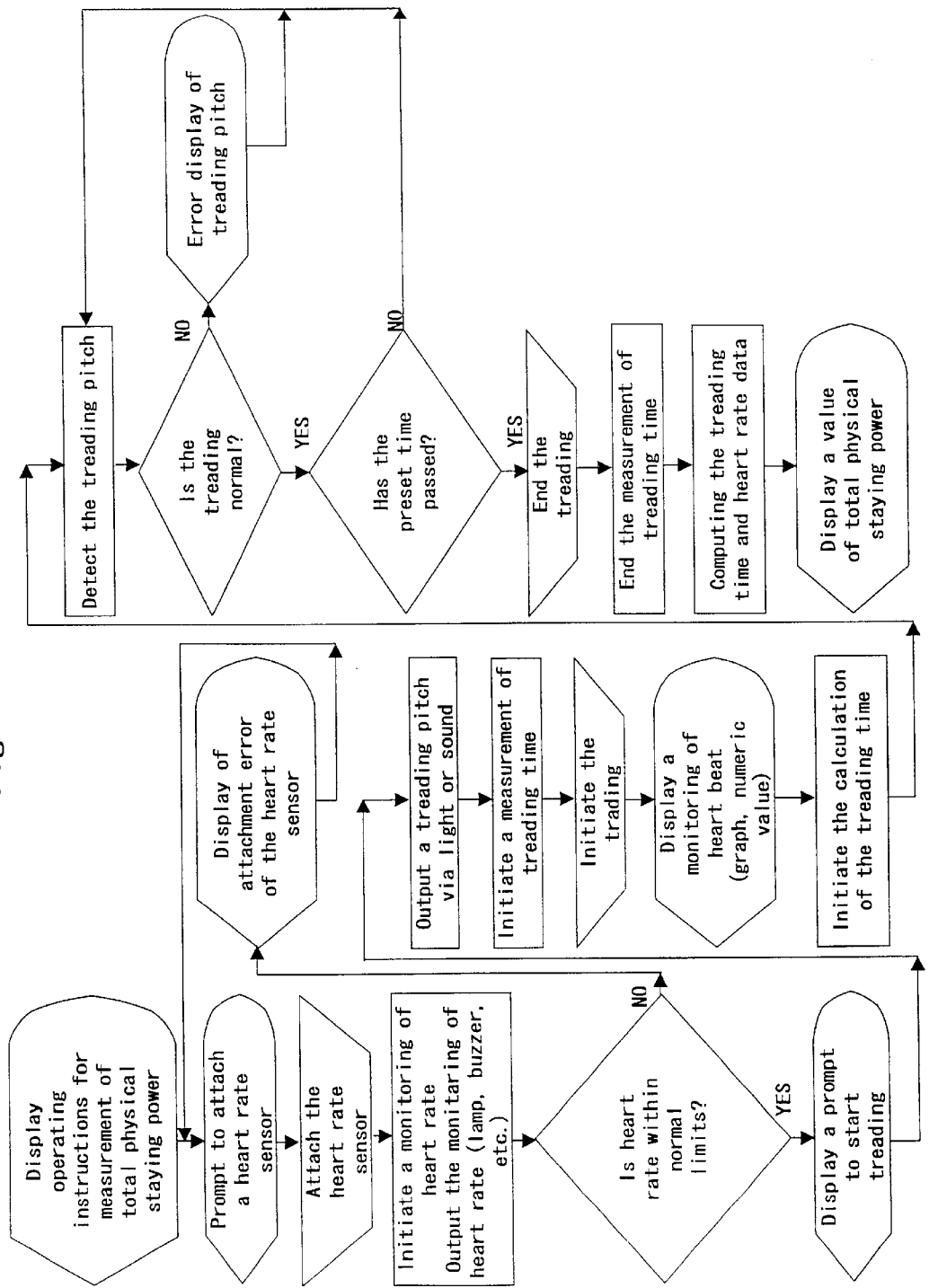
FIG. 13 is a detailed flowchart of the measuring procedure.

Then, in the total physical staying power measuring procedure of the step S6, the body fat of the person to be measured is measured and stored by the body fat measuring part 5. An example of the detailed procedure is shown in FIG. 13.

Figure 14:
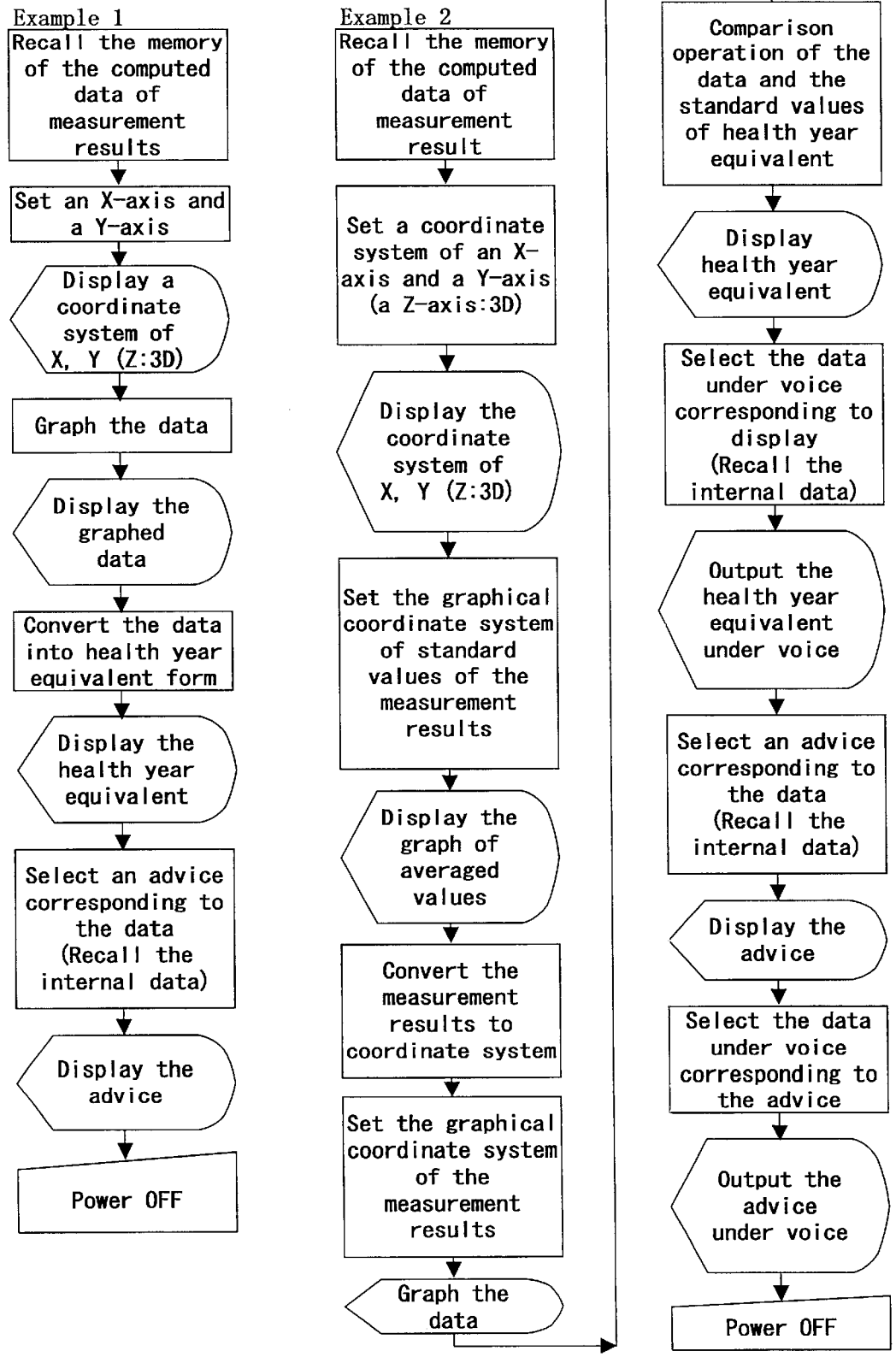
FIG. 14 is a detailed flowchart of the measuring procedure.

Then, in the arithmetical operation procedure of the step S7, the character data and graphic data for display are computed on the basis of the measured data and are displayed in the step S8. An example of the detailed procedure is shown in FIG. 14.

Figure 15:
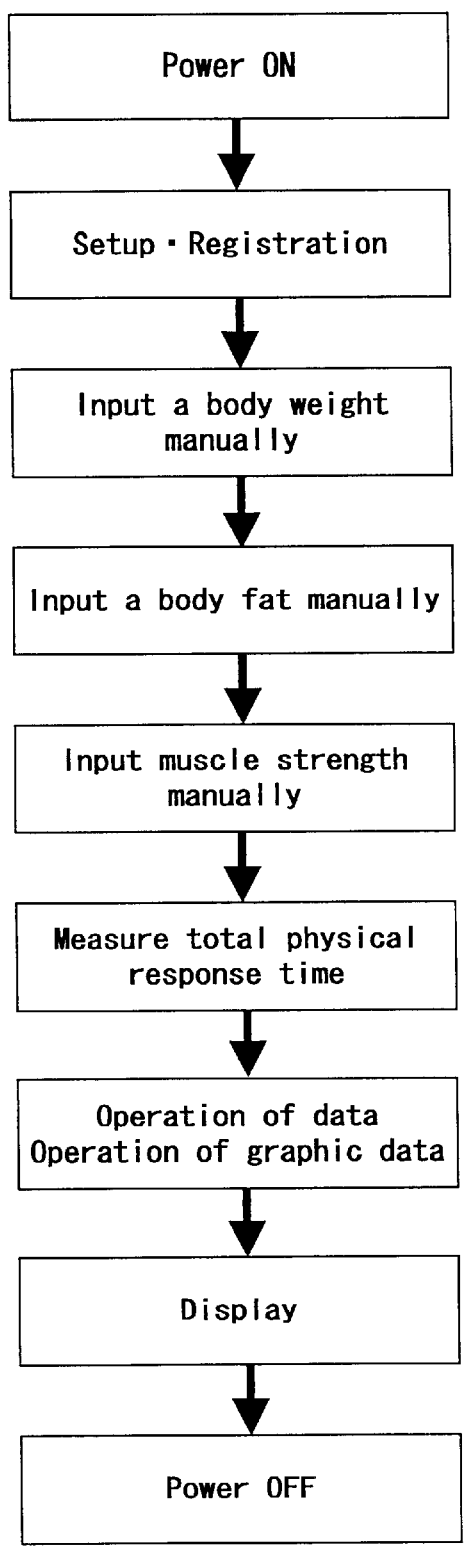
FIG. 15 is a detailed flowchart of the measuring procedure.
Figure 16:
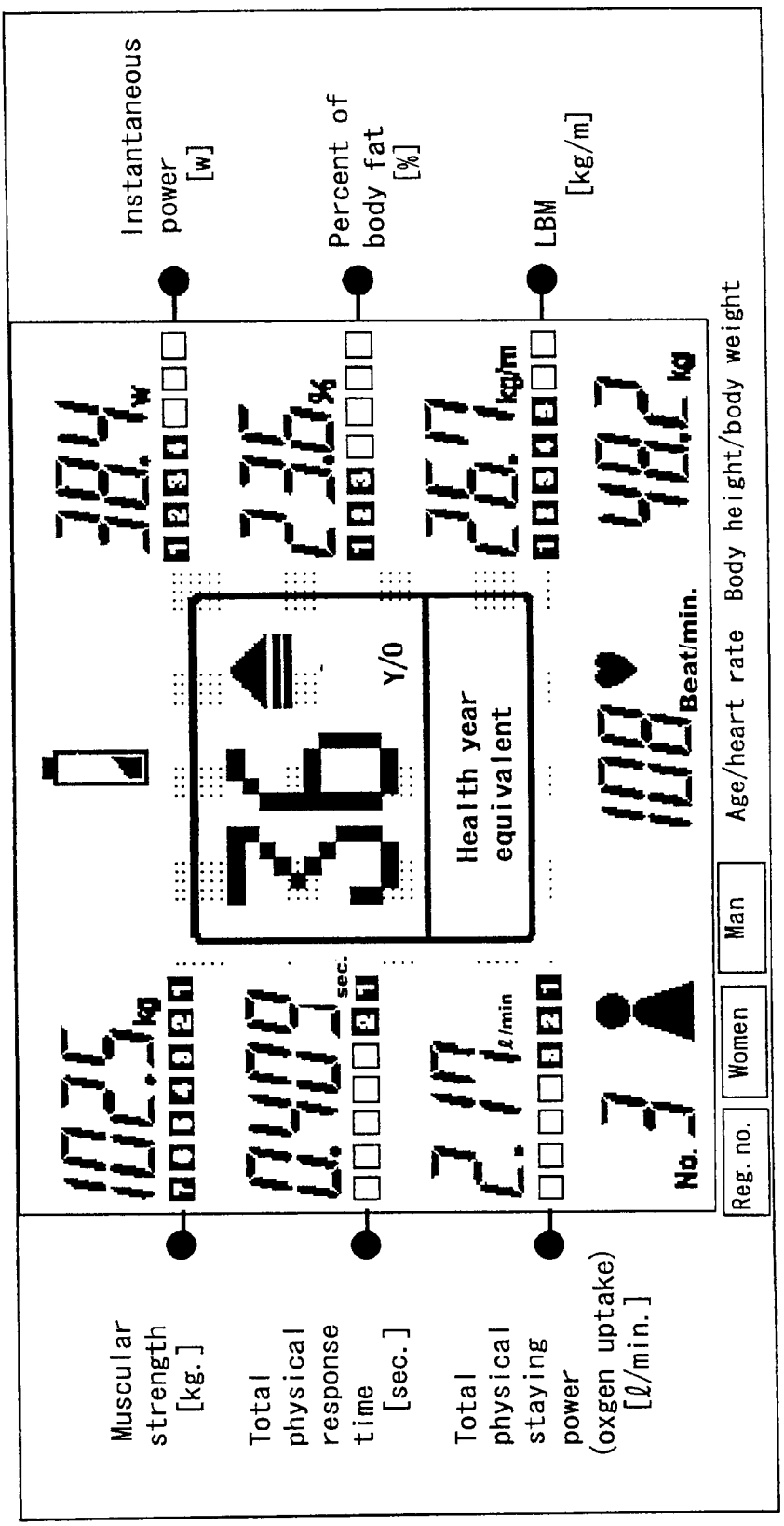
FIG. 16 is an illustration of an example of measurements in the display screen.
Figure 17:
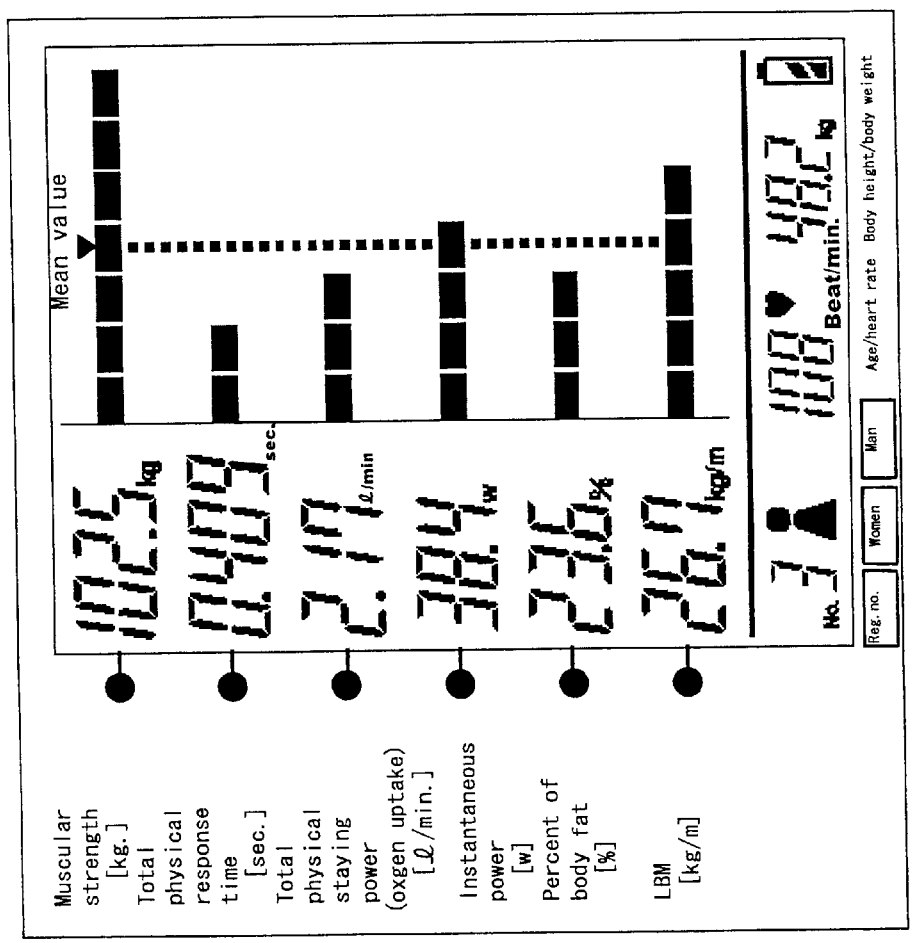
FIG. 17 is an illustration of an example of measurements in the display screen.
Figure 18:
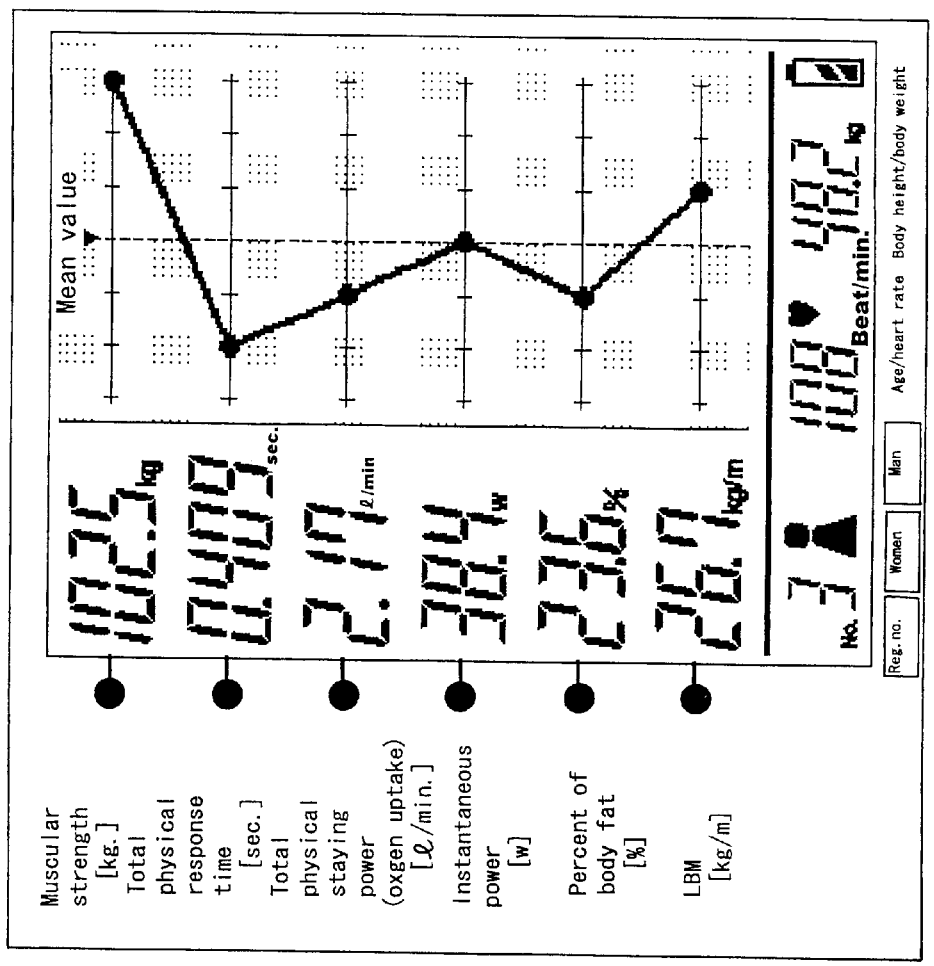
FIG. 18 is an illustration of an example of measurements in the display screen.
Figure 19:
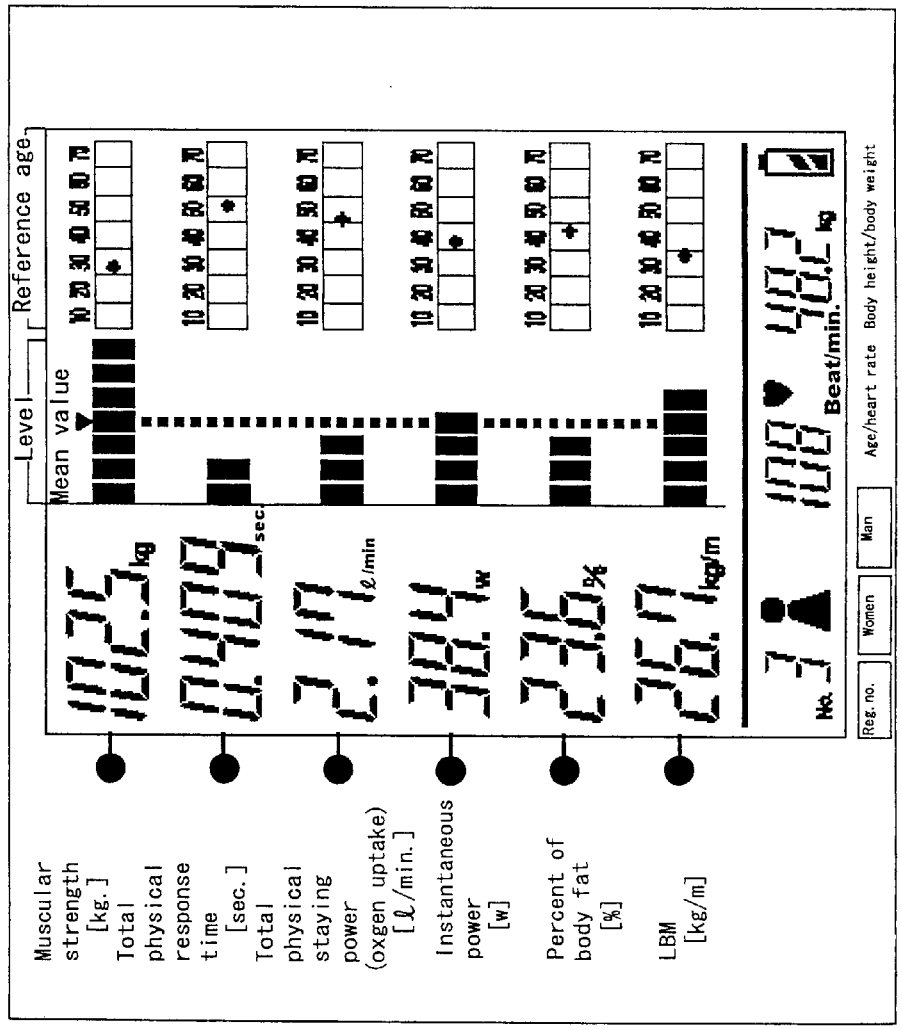
FIG. 19 is an illustration of an example of measurements in the display screen.

Modification may effectively be made, for example, by omitting the measurements of body weight, body fat, muscle strength/muscle staying power and total physical staying power, but instead inputting the indicators thereof (body weight, body fat and muscle strength) manually by use of the group of switches in the display control part, so as to measure the total physical response time only, as shown in FIG. 15.

Figure 20:
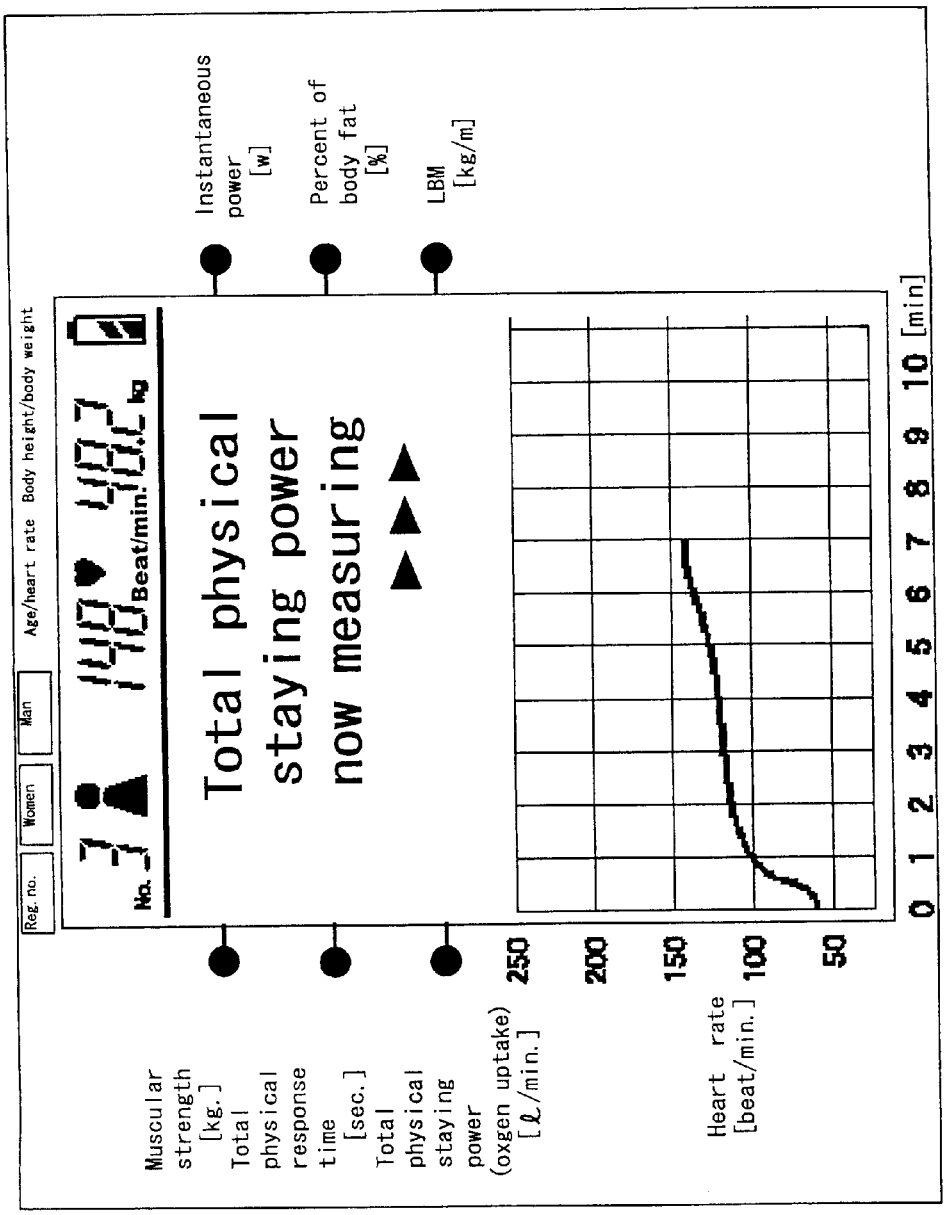
FIG. 20 is an illustration of an example of measurements in the display screen.

Referring to FIGS. 16–19, there are shown examples of the display screens displaying the measured results. FIG. 20 shows an example of the screen shot displaying "Now measuring the total physical staying power".

The device may be constructed to display a targeted value of the body fat and some advice or suggestion on how to take exercise or fitness.

The outputs of measurement results, indicators and advice may be presented on the screen in the form of characters and graphics. They may alternatively be presented in the form of synthetic voice through speakers or earphones.

Referring now to FIGS. 21–28, there are shown perspective views of various different embodiments.

Figure 21A:
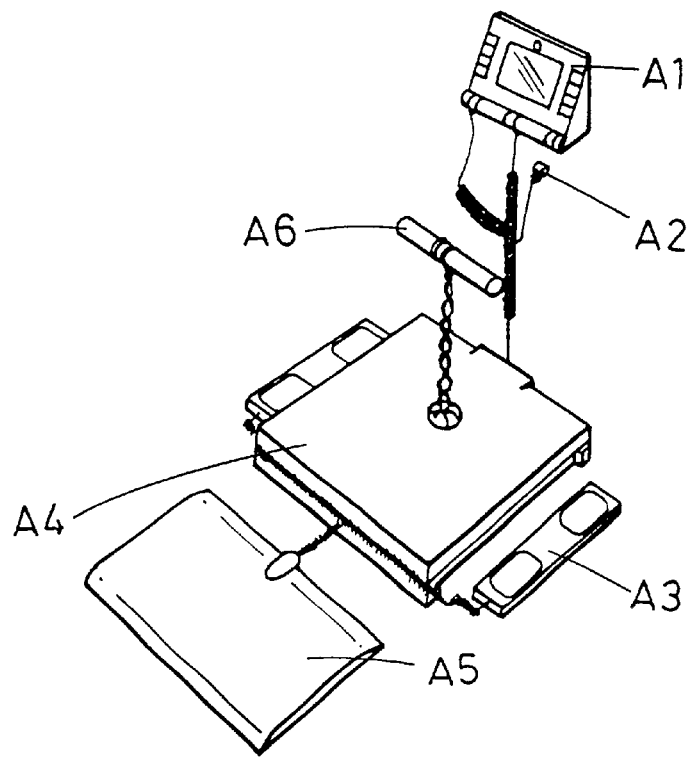
FIG. 21 is a perspective view of another preferred embodiment.

In FIG. 21(A), A1 designates an operation display part, A2 designates a heart beat sensor for measuring the heart rate, A3 designates electrodes for measuring the body fat, A4 designates a measuring platform of the body weight measuring part, and A5 designates a jumping board for use in measuring the total physical response time. A handgrip A6 for use in measuring the muscle strength is coupled to a chain drawn out from an opening in the measuring platform A4.

Figure 21B:
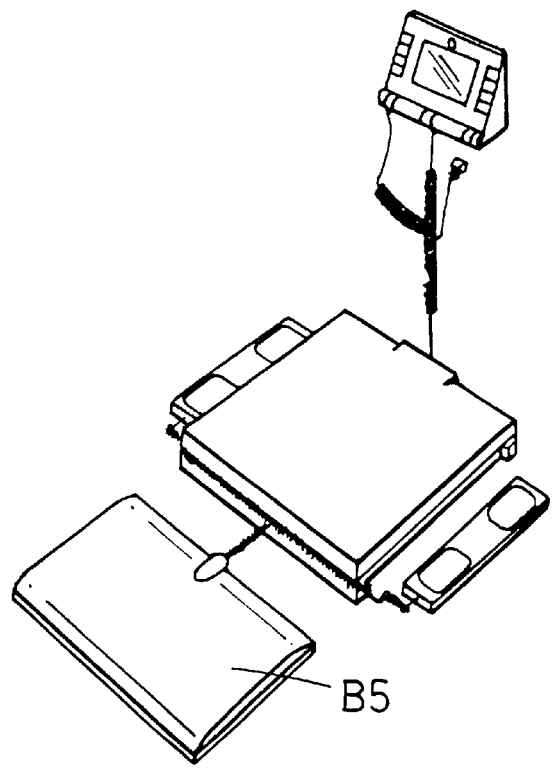

FIG. 21(B) shows a variant wherein the load sensor of the body weight measuring part is used both for the function of the load sensor and the function of measuring the muscle strength. This sensor can measure the treading load on a measuring platform B5 in the jump to determine the muscle strength.

Figure 22A:
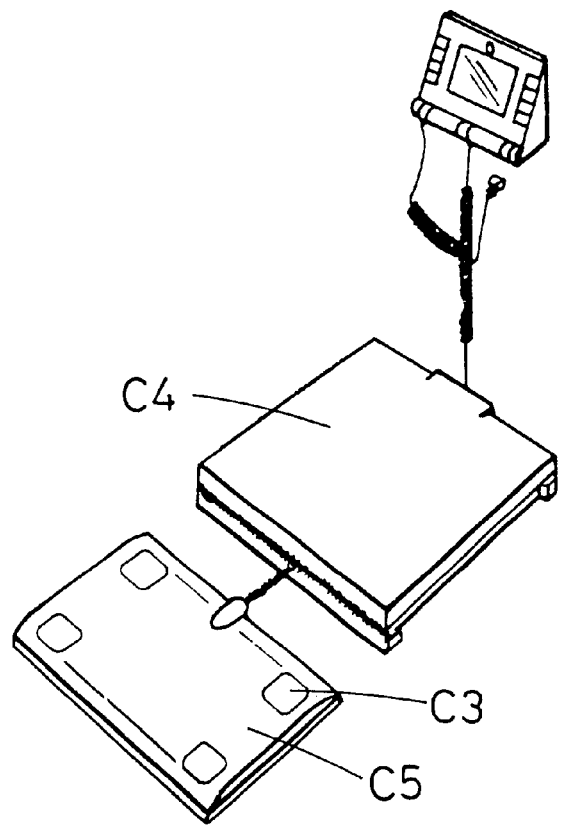
FIG. 22 is a perspective view of another preferred embodiment.

FIG. 22(A) shows another embodiment wherein electrodes C3 for measuring the body fat are arranged on a jumping board C5 or on a measuring platform C4.

Figure 22B:
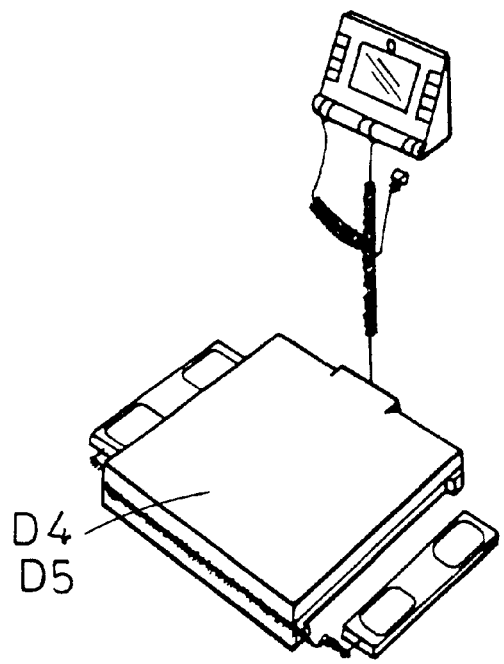

FIG. 22(B) shows a variant having no jumping board or having a measuring platform D4 doubled as a jumping board D5.

Figure 23A:
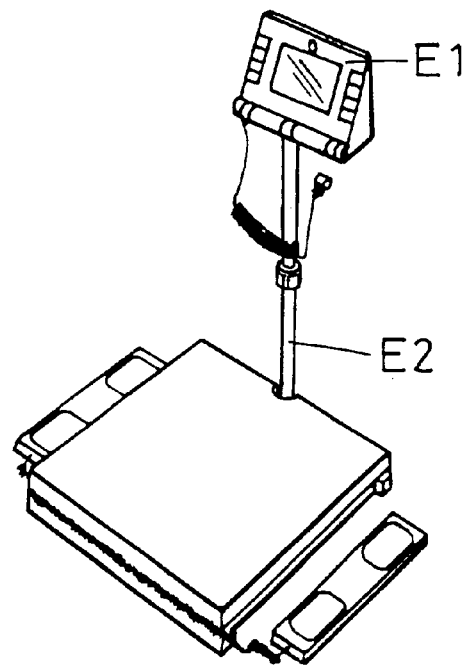
FIG. 23 is a perspective view of another preferred embodiment.

FIG. 23(A) shows an arrangement wherein an operation display part E1 is secured to an extensible pole E2 vertically extending from a base portion of the body weight measuring part.

Figure 23B:
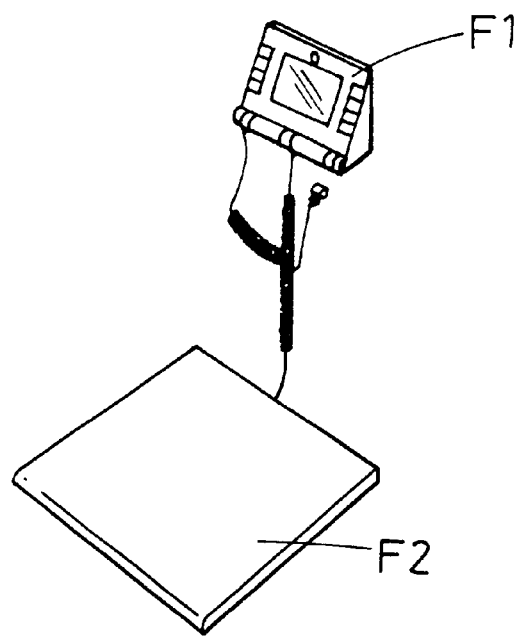

FIG. 23(B) shows a yet another embodiment which is structured to manually enter the body weight, body fat and muscle strength for the sake of simplified function and has a jumping board F2 and an operation display part F1. In this embodiment, the body weight and the body fat are manually entered to determine a value of the LBM and the total physical staying power is determined by the arithmetic operation on the basis of the correlation expression.

FIG. 24 shows an example which is structured to include a handgrip or equivalent of the operating means 32 such as the chain coupled to the load sensor 31 so that the person to be measured who mounts the measuring platform 30 can pull up the handgrip or equivalent to measure the difference between the body weight and the back strength. The back strength can be measured by the sum of the body weight and said difference.

FIGS. 25 and 26 are examples which are structured to measure grip strength by deforming the load sensor 31 by gripping.

FIG. 27 is a construction example which is formed to have a step G for treading exercise.

FIG. 28 is an example which is structured to include acceleration-sensors-contained plummets H to be fitted to the ankles, so as to measure the kinetic momentum.

In addition to the embodiments illustrated above, various variants may be made, for example, by being modified to manually enter only the body weight or the body weight and the body fat.

Further, modification may be made to add the body height measuring function.

What is claimed is:

1. A health indicator measuring device comprising:
   a means for inputting data of body weight, body fat and body height;
   an arithmetical operation means for computing data of a lean body per body height or data of body fat per body height from the data input; and
   an output means for outputting computed data of a lean body per body height or computed data of body fat per body height.

2. A health indicator measuring device according to claim 1, wherein the means for inputting data, the arithmetical operation means and the output means are integrally provided.

3. A health indicator measuring device, comprising:
   a physical function measuring means for measuring a qualitative aspect or a quantitative aspect of muscle of a person to be measured,
   an arithmetical operation means for computing function of the body on the basis of the physical function of the body measured by said physical function measuring means; and
   an output means for outputting a function indicator computed by said arithmetical operation means.

4. The health indicator measuring device according to claim 3, wherein said output means outputs the function indicator computed on the basis of the physical function of the body measured in relation to age.

5. The health indicator measuring device according to claim 3, wherein the output means is capable of comparing the function indicator computed on the basis of the physical function of the body measured with preset standard indicators and to output data of the difference therebetween.

6. The health indicator measuring device according to claim 3, wherein the output means is capable of comparing the function indicator computed on the basis of the physical function of the body measured with preset standard indicators at selected ages and to output an equivalent age to a closest indicator as an indicator of a health year equivalent.

7. The health indicator measuring device according to claim 3, wherein the output means has the capability of outputting advice data on practical fitness for health related to the physical function of the body measured.

8. The health indicator measuring device according to claim 3, wherein said physical function measuring means measures muscle strength of a person to be measured.

9. The health indicator measuring device according to claim 8, wherein said physical function measuring means measures at least one of instantaneous muscle power and muscle staying power.

* * * * *